Figure 1:
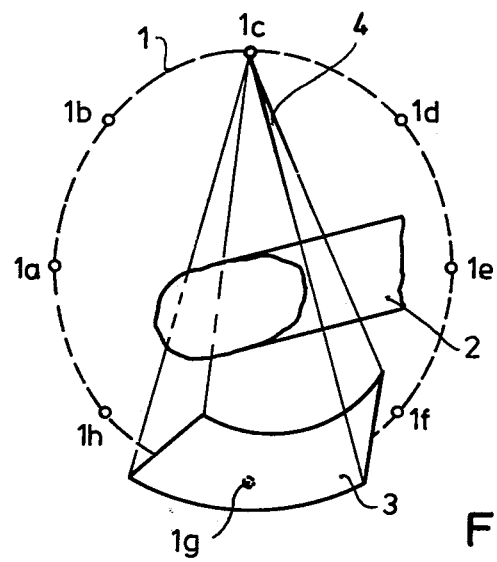

United States Patent [19]

Kowalski

[11] 4,204,124

[45] May 20, 1980

[54] DEVICE FOR MEASURING RADIATION ABSORPTION IN A THREE-DIMENSIONAL OBJECT

[75] Inventor: Günter Kowalski, Rellingen, Fed. Rep. of Germany

[73] Assignee: U.S. Philips Corporation, New York, N.Y.

[21] Appl. No.: 897,448

[22] Filed: Apr. 18, 1978

[30] Foreign Application Priority Data

Jun. 14, 1977 [DE] Fed. Rep. of Germany ....... 2726635

[51] Int. Cl.$^2$ .............................................. A61B 6/00
[52] U.S. Cl. ................................ 250/445 T; 250/360
[58] Field of Search ............................ 250/44 ST, 360

[56] References Cited

U.S. PATENT DOCUMENTS 4,002,917  1/1977  Mayo .................................. 250/360

Primary Examiner—Alfred E. Smith
Assistant Examiner—T. N. Grigsby
Attorney, Agent, or Firm—Thomas A. Briody; Jack Oisher; Jack E. Haken

[57] ABSTRACT

A device for reconstructing the absorption distribution in a three-dimensional body. The body to be examined is imaged from two groups of radiation source positions. Each group of radiation source positions is situated on an arc of a circle around the axis of rotation, and the acrs of a circle determine the dimensions of the region in which the absorption distribution is reconstructed. The detector device is disposed between the two arcs of a circle.

3 Claims, 6 Drawing Figures

DEVICE FOR MEASURING RADIATION ABSORPTION IN A THREE-DIMENSIONAL OBJECT

The invention relates to a device for measuring radiation absorption in a three-dimensional object comprising at least one two-dimensional detector device which measures a series of local intensity values of a radiation beam which passes through the object. The object is irradiated by a radiation source from a large number of positions which are situated in a first plane and a second.

Computer tomography apparatus is known in which the absorption distribution in a two-dimensional plane is reconstructed (German Offenlegungsschrift No. 24 42 809). Therein, the object is irradiated by an X-ray source with a radiation beam which is narrow in a direction perpendicularly to a plane of examination, said beam irradiating the complete object in at least one direction and being measured by a detector device which is situated opposite the source in the plane of examination. The X-ray source detector system is rotated about an axis which extends perpendicular to the plane of examination, the output signals of the detector device thus obtained are used to reconstruct the absorption distribution in the plane.

With such an apparatus, however, the absorption distribution of only one or (if a second detector device is provided) at the most two adjacent slices of a three-dimensional object can be measured at one time. If adjacent slices are successively scanned by means of such an apparatus, relative displacements are liable to occur therebetween, due to movements of the body, so that the absorption distributions reconstructed on the basis of the detector output signals are not in registration.

The term "two dimensional detector device" as used herein means a detector whose output signals characterize the distribution of radiation intensity in two orthogonal directions. Such a detector is described, in connection with a device which measures radiation absorption in a three dimensional object, in an article by R. E. Sturm et al in "Cardiovascular Imaging and Image Processing, Theory and Practice 1975", Vol. 72, pages 103–122. Such detectors may be contrasted to detectors described in German Offenlegungsschrift No. 2442809 which, because of the finite size of the detector elements, extend in two dimensions but whose output signals are independent of intensity distributions along more than one direction.

The prior art device for measuring the absorption distribution in a three-dimensional object as described in the article by R. E. Sturm et al gives rise to reconstruction problems if the aperture angle of the radiation beam is too large in a direction perpendicular to the source plane. Moreover, measuring errors of the detector elements present in the detector device adversely influence the reconstruction.

The present invention has for its object to provide a device for measuring the absorption distribution in a three-dimensional object in which the reconstruction problems as well as the effect of measuring errors of the detector elements on the reconstruction of the absorption distribution are mitigated.

In accordance with the invention a detector is bounded, on one side by a first plane and on the other side by a second plane which is spaced from the first plane and which extends parallel thereto and the object irradiated from a large number of positions which are situated in the first and second planes.

A further embodiment of the device in accordance with the invention comprises a support which is rotatable about an axis of rotation which extends perpendicular to both planes and which supports a first radiation source and a first detector device as well as, a second radiation source and a second detector device shifted in the axial direction with respect thereto, the two detector devices are bounded in the axial direction by the first plane extending through the first radiation source and by the second plane which extends parallel thereto and through the second radiation source.

An embodiment of the device in accordance with the invention will be described in detail hereinafter with reference to the accompanying drawing.

Figure 2:
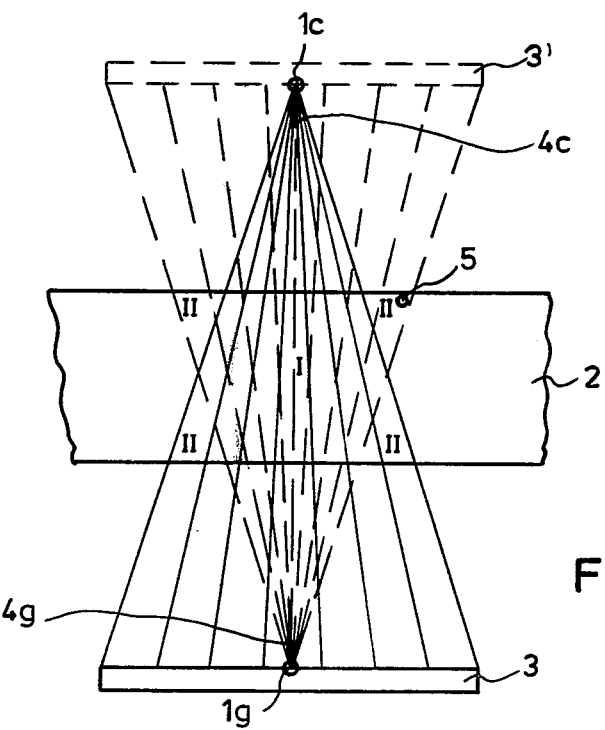
Figure 3:
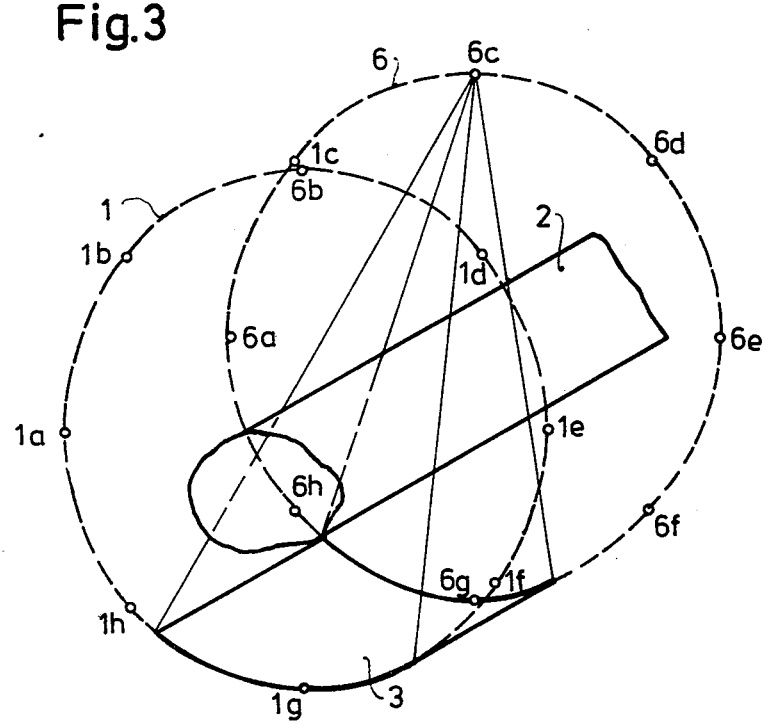
Figure 4:
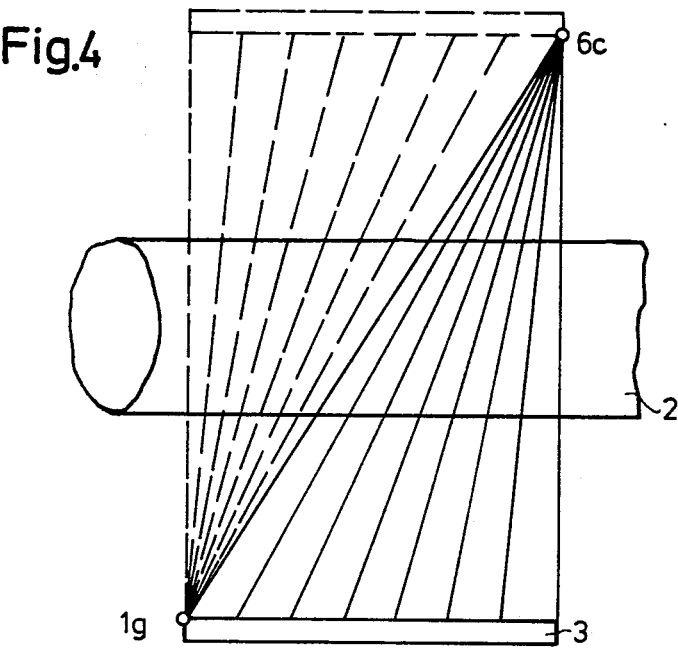
Figure 5:
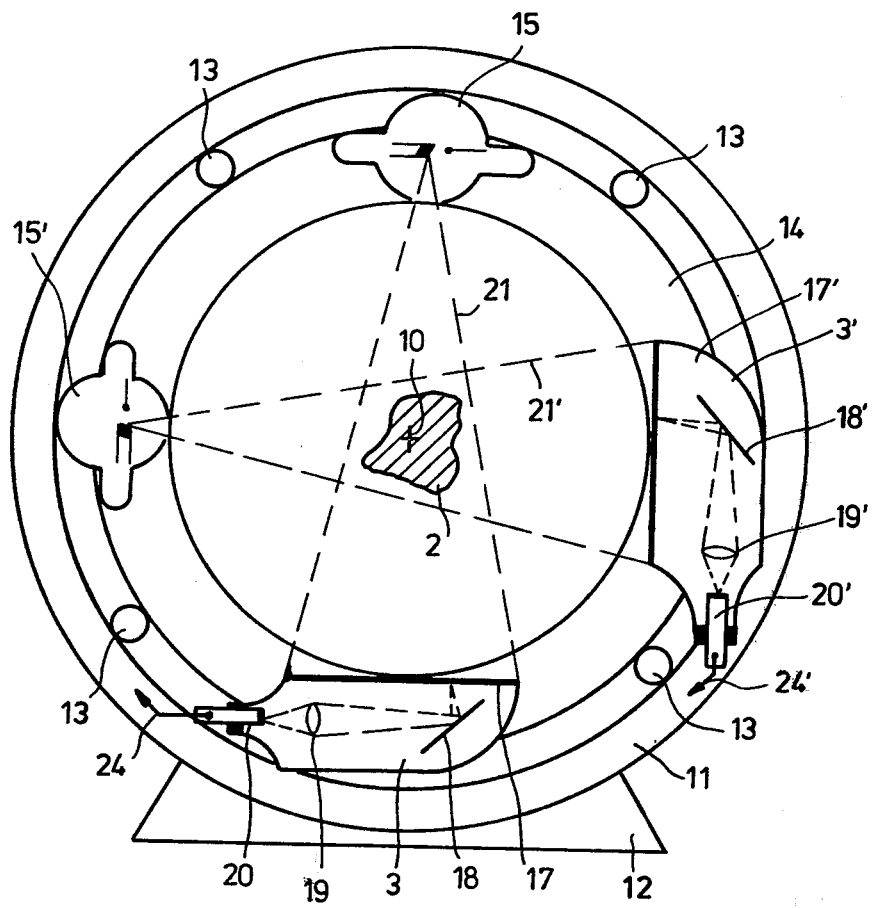
Figure 6:
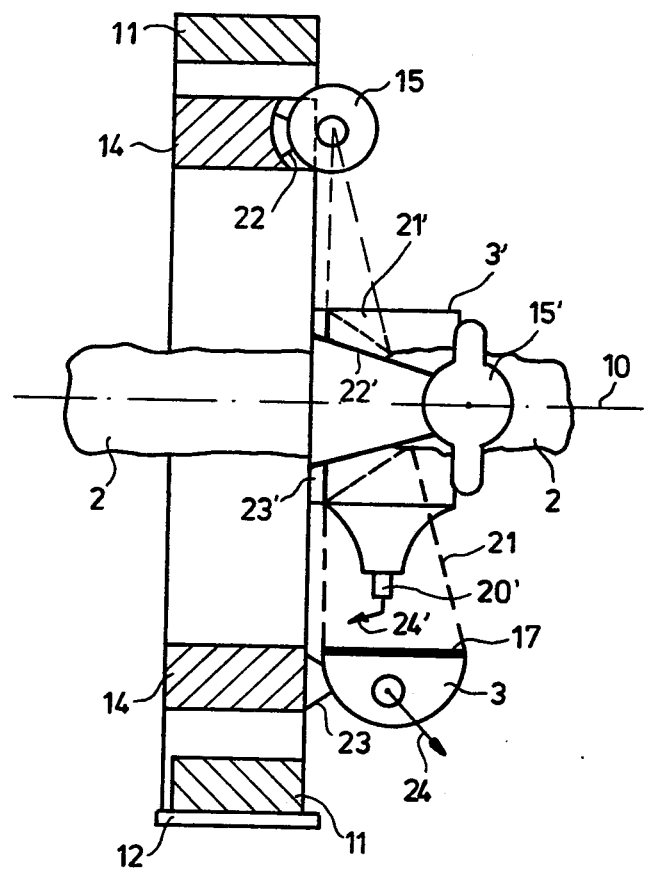

FIG. 1 is a perspective view of the geometrical configuration of a known device, FIG. 2 shows the geometrical configuration of the known device in a plane perpendicular to the first plane, FIG. 3 is a perspective view of the geometrical configuration in accordance with the invention, FIG. 4 shows the geometrical configuration in accordance with the invention, perpendicular to both planes, FIG. 5 is a diagrammatic front view of an embodiment in accordance with the invention, and FIG. 6 is a side elevation of this embodiment.

The reference numeral 1 in FIG. 1 denotes an arc of a circle on which are situated the positions $1a \ldots 1h$ wherefrom a body Z is irradiated during examination. In the device described in the article by R. E. Sturm, the radiation is produced by a large number of radiation sources (X-ray tubes) which are situated in the positions $1a \ldots 1h$; however, use can alternatively be made of a single radiation source which is successively positioned in the positions $1a \ldots 1h$. For the sake of simplicity, the drawing shows only eight different positions; however, a substantially larger number of positions is required in order to obtain adequate spatial resolution.

A radiation beam projected from the position $1c$ of a radiation source (not shown) in FIG. 1 is denoted by the reference 4. This beam is pyramid-shaped and the plane in which the arc of a circle 1 is situated is a symmetry plane of the pyramid. The radiation beam is measured by a two-dimensional detector device 3 which is arranged opposite the position $1c$. This detector device is curved around the central axis of the arc of a circle 1 and extends perpendicular to the plane enclosed by the arc of a circle. FIG. 2 shows the geometrical configuration in a plane which is perpendicular to the arc of a circle and which extends through the center of the body 2 to be examined. The radiation beam $4c$, stopped in the position $1c$ as well as the detector device 3 being denoted by uninterrupted lines, while the radiation beam $4g$ stopped in the position $1g$ and the associated detector position $3'$ are denoted by broken lines. It is clearly shown that there are regions II which are only very weakly irradiated by radiation and a region I which is irradiated by approximately double the quantity of radiation. Points situated outside this region, for example, the point 5, are measured in only one position of the radiation source (N), in this case in the position $1g$, and radiation from the other positions does not contact this point. Object details situated at this area can substantially impede reconstruction, because only little information is obtained as regards these details. If, moreover, measuring errors occur, the reconstruction will be incorrectly determined for a prolonged period of time.

FIGS. 3 and 4 show the geometrical relationships in a device in accordance with the invention. Instead of one arc of a circle, two arcs of a circle 1 and 6 which are situated in planes extending parallel to each other and which have been shifted perpendicularly to their planes with respect to each other are provided. The body 2 to be examined is irradiated from positions which are situated on the arc of a circle 1 (positions 1a to 1h) as well as from positions on the arc of a circle 6 (positions 6a to 6h). The detector device 3 is proportioned and arranged, in a direction perpendicular to the planes formed by the two arcs of a circle 1 and 6, so that the device is bounded by said planes. The radiation beam emitted from the various positions of the radiation source on the arcs of a circle 1 and 6, is then also shaped as a pyramid having a square base, but this pyramid is not symmetrical to the planes, or a plane extending parallel thereto, containing the arcs of a circle 1 and 6, as is particularly shown in FIG. 4. One side of this pyramid-shaped radiation wedge then coincides with the plane containing the arc of a circle 1 or 6.

FIG. 4 shows the radiation wedges (solid line and broken line, respectively) produced when the body 2 is irradiated from the positions 6c and 1g. These positions have been rotated 180° with respect to each other relative to the central axis extending perpendicularly through both arcs of a circle, and shifted over the distance between the two planes with respect to each other. It is clearly shown that a thick slice of the object is homogeneously irradiated to a high degree, and that each point in the examination region, which may be defined as a cylinder which is coaxially arranged within the arcs of a circle 1 and 6 and which comprises flat end faces, is covered by the radiation wedge stopped either in the position 1g or the position 6c. Such a pair of positions, shifted 180° with respect to each other and arranged on the two arcs of a circle, can be given for a large number of directions, so that the same radiation distribution is obtained as shown in FIG. 4.

As a result of the homogeneous irradiation, the amount of information obtained as regards the absorption of a point within the examination region is highly independent of the position of this point in the examination region. This substantially facilitates the reconstruction and, moreover, measuring errors are less significant for reconstruction. A further advantage consists in that the examination region is a space which can be simply defined mathematically (a cylinder comprising flat end faces), so that the object is described by a cylindrical coordinate system upon reconstruction.

It is not necessary that a position exists on one arc of a circle for each position on the other arc of a circle which has been rotated exactly 180° with respect to the central axis. The configuration shown in FIG. 4 is not completely obtained in that case, because there is no directly opposite position, but there are always two positions which are situated almost opposite each other. Because generally a large multitude of positions must be present on an arc of a circle, incorrect measurements are not caused thereby. Nor is not necessary either for the positions to be distributed over the entire circumference of both arcs of a circle; it is generally sufficient that only a part of an arc of a circle, which must be larger than one half circle, is occupied by such positions, as long as for each position on the one arc of a circle a complementary position on the other arc of a circle can be given, i.e. a position shifted approximately 180° with respect thereto.

The irradiation of the object 2 from the various positions can in principle be realized with a radiation source arranged in each position. However, this is very expensive. On the other hand, irradiation can also be realized with a single radiation source which is successively arranged, for example, first in the various circle positions on the arc of a circle 1 and subsequently in the various positions on the arc of a circle 6. When changing over from the one to the other arc of a circle, collimation will also have to be changed in order to obtain the relationships shown in FIG. 4.

An effective compromise between these two possibilities consists in the provision of a separate radiation source for each arc of a circle, these sources being moved together about an axis of rotation so as to successively pass through the positions on an arc of a circle. The collimation of the radiation wedges, adapted to the dimensions of the detector device, can then be maintained in all positions of each of the two radiation sources. An embodiment of this kind is diagrammatically shown in the FIGS. 5 and 6.

A supporting ring 14 is journalled to be rotatable in known manner about its central axis 10, by way of bearings 13 in a bearing ring 11 which is rigidly connected to a base 12. A first X-ray source 15 is mounted on a holder 22 which is connected to the supporting ring 14. Opposite thereto there is arranged a first detector device 3 which is also connected to the supporting ring 14 via a holder 23, so that the X-ray source 15 can be rotated about the axis 10 together with the detector device 3.

A second X-ray source is mounted, shifted through 90° with respect to the first source, on the supporting ring via a holder portion 22' which is substantially longer than the holder portion 22 supporting the first X-ray source 15. Opposite thereto there is arranged a second detector device 3' which is also connected to the supporting ring 14 via a holder 23'. The two detector devices 3 and 3' extend between the planes which extend through the centers (i.e. the focal points) of the X-ray sources 15 and 15', perpendicular to the axis of rotation 10 (FIG. 6). The radiation of the X-ray sources 15 and 15' is collimated by collimeters (not shown) so that radiation cones 21 and 21' are formed which cover the overall effective measuring area of the detector devices 3 and 3' respectively.

As is known from the article by R. E. Sturm (page 110, notably FIG. 5), each of the two detector devices comprises a flat fluorescent screen 17, 17', respectively, wherebehind a mirror 18, 18' respectively, is arranged; this mirror projects the visible image, being dependent of the local intensity of the radiation, via a lens system 9, 9' respectively, onto the target of a television camera 20, 20' respectively, for example, of the Isokon type. An image intensifier may also be arranged in the beam path.

The television camera 20 and 20', respectively, linewise scan the luminescent surface of the fluorescent screen 17, 17', so that the output signal derived from the signal electrode 24, 24', represent the intensity (and hence also the absorption) through the object 2 as a function of the position (in two mutually perpendicular directions).

Instead of such a detector device, use can alternatively be made of a detector device which consists of a large number of adjacent rows of detectors, each of which comprises a large number of individual detector elements.

What is claimed is:

1. A device for measuring radiation absorption in a section of a three dimensional object which lies between a first plane and a parallel second plane comprising:

radiation source means which project wedge-shaped beams of radiation from a plurality of positions in said first plane and from a plurality of positions in said second plane, through said object, to illuminate a detector area bounded by said first plane and second plane and a two-dimensional radiation detector disposed on said detector area.

2. A device for measuring radiation absorption in a section of a three dimensional object which lies between a first plane and a parallel second plane comprising:

a two-dimensional radiation detector bounded by said first plane and said second plane;

first radiation source means which project radiation beams from a plurality of positions in said first plane, through said object, to said detector and second radiation source means which project radiation beams from a plurality of positions in said second plane, through said object, to said detector.

3. A device for measuring radiation absorption in an object comprising:

a support rotatable about said object on an axis of rotation;

a first radiation source disposed on said support and rotatable therewith in a first plane lying perpendicular to said axis;

a second radiation source disposed on said support and at least axially displaced from said first source, said second source being rotatable with said support in a second plane lying parallel to said first plane;

a first two dimensional detector disposed on said support, opposite said first source to receive radiation therefrom; and a second two dimensional detector disposed on said support, opposite said second source, to receive radiation therefrom;

said first and second detectors each being bounded in the axial direction by said first plane and said second plane.

* * * * *